US008834501B2

(12) United States Patent
Slater

(10) Patent No.: US 8,834,501 B2
(45) Date of Patent: Sep. 16, 2014

(54) SCISSORS ASSEMBLY

(75) Inventor: Charles R. Slater, Fort Lauderdale, FL (US)

(73) Assignee: Slater Endoscopy, LLC, Miami Lakes, FL (US)

(*) Notice: Subject to any disclaimer, the term of this patent is extended or adjusted under 35 U.S.C. 154(b) by 488 days.

(21) Appl. No.: 13/299,467

(22) Filed: Nov. 18, 2011

(65) Prior Publication Data

US 2012/0116434 A1 May 10, 2012

Related U.S. Application Data

(63) Continuation of application No. 12/335,656, filed on Dec. 16, 2008, now Pat. No. 8,128,649.

(51) Int. Cl.
*A61B 17/3201* (2006.01)
*A61B 17/32* (2006.01)

(52) U.S. Cl.
CPC ..... *A61B 17/3201* (2013.01); *A61B 17/320016* (2013.01)
USPC .......................................... 606/174; 606/170

(58) Field of Classification Search
CPC .................... A61B 17/320016; A61B 17/3201
USPC ............ 606/170, 174, 205, 210; 30/244, 249, 30/296.1
See application file for complete search history.

(56) References Cited

U.S. PATENT DOCUMENTS

| 714,087 | A | 11/1902 | Woods |
| 4,153,992 | A | 5/1979 | Gunneman |
| 4,877,026 | A | 10/1989 | De Laforcade |
| 5,157,837 | A | 10/1992 | Rose |
| 5,275,607 | A | 1/1994 | Lo et al. |
| 5,314,440 | A | 5/1994 | Shapiro |
| 5,320,636 | A | 6/1994 | Slater |
| 5,334,198 | A | 8/1994 | Hart et al. |
| 5,350,391 | A | 9/1994 | Iacovelli |
| 5,355,585 | A | 10/1994 | Tepic |
| 5,356,408 | A | 10/1994 | Rydell |
| 5,395,386 | A | 3/1995 | Slater |
| 5,562,693 | A | 10/1996 | Devlin et al. |
| 5,584,845 | A * | 12/1996 | Hart .............................. 606/174 |
| 5,797,939 | A * | 8/1998 | Yoon .............................. 606/167 |

(Continued)

FOREIGN PATENT DOCUMENTS

| CH | 649911 | 6/1985 |
| EP | 00589454 | 3/1994 |
| GB | 2239831 | 6/1990 |
| JP | 9140720 | 3/1997 |

*Primary Examiner* — Thomas McEvoy
*Assistant Examiner* — Julie A Szpira
(74) *Attorney, Agent, or Firm* — Gordon & Jacobson, PC

(57) ABSTRACT

An endoscopic scissor instrument includes an elongate hollow member, an actuator that moves axially through the hollow member, and first and second scissor blades with respective cutting surfaces. At least one of the scissor blades is rotatably coupled to the hollow member adjacent its distal end. At least one of the scissor blades includes a base supporting a resilient leaf-spring portion that includes a respective cutting edge. The resilient leaf-spring portion extends from the base in a cantilevered arrangement and generates a spring force acting on the respective cutting edge such that in a loaded state there is an automatic preload force imparted between the cutting edges of the scissor blades to maintain a consistent and continuous mating force between the two opposed sharpened cutting edges preferably over the complete range of rotational movement of the scissor blades.

24 Claims, 10 Drawing Sheets

(56) References Cited

U.S. PATENT DOCUMENTS

| | | |
|---|---|---|
| 5,908,420 A | 6/1999 | Parins et al. |
| 5,911,736 A | 6/1999 | Dingler et al. |
| 5,984,938 A * | 11/1999 | Yoon .............................. 606/170 |
| 6,086,606 A | 7/2000 | Knodel et al. |
| 6,096,059 A | 8/2000 | Kuzma |
| 6,168,605 B1 | 1/2001 | Measamer et al. |
| 6,176,866 B1 | 1/2001 | Christoudias |
| 6,270,508 B1 * | 8/2001 | Klieman et al. ............... 606/147 |
| 6,371,956 B1 | 4/2002 | Wilson et al. |
| 2004/0098007 A1 * | 5/2004 | Heiss ............................ 606/174 |

* cited by examiner

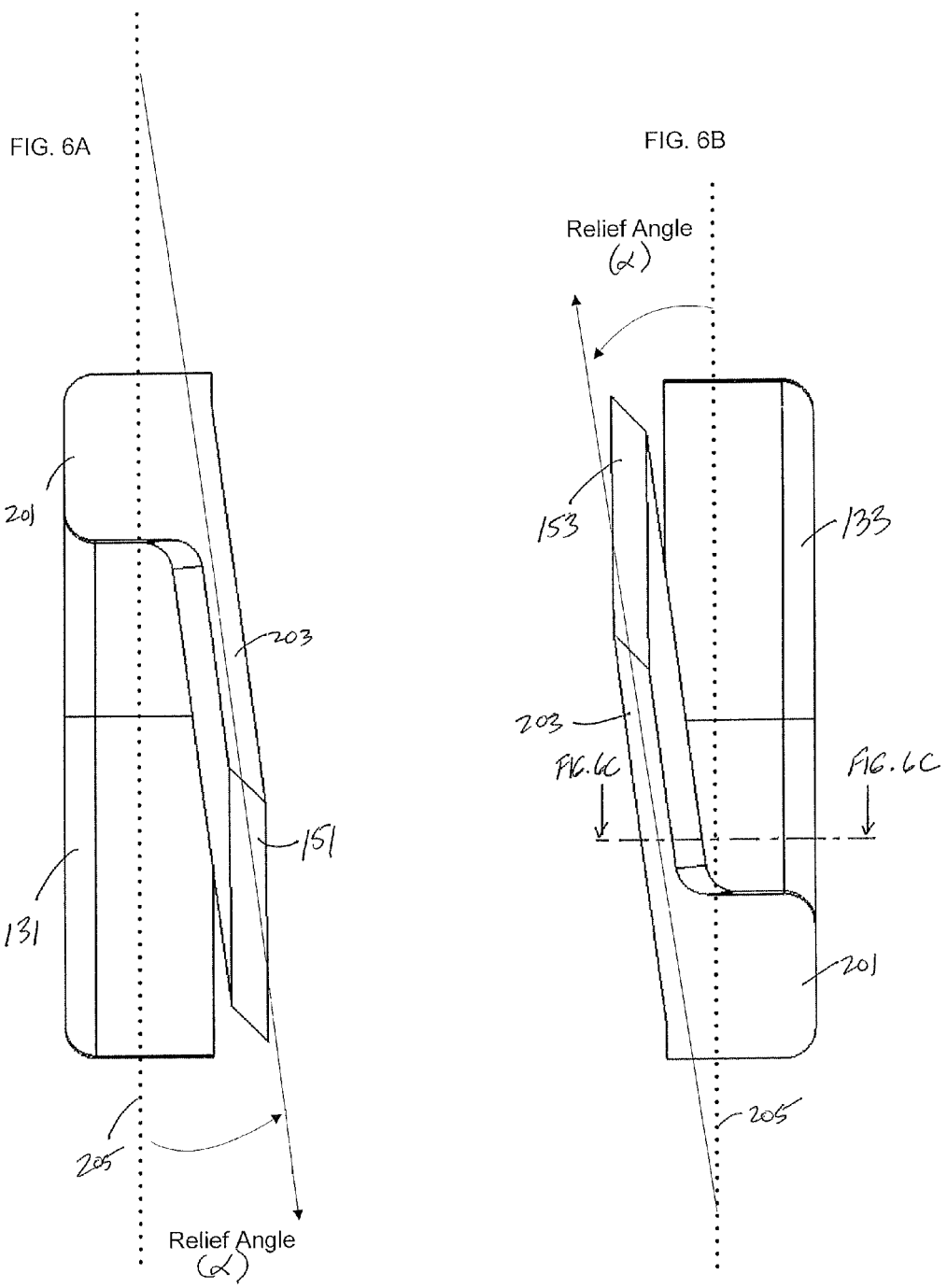

SCISSORS ASSEMBLY

CROSS-REFERENCE TO RELATED APPLICATION

This application is a continuation of U.S. Ser. No. 12/335,656, filed Dec. 16, 2008, now U.S. Pat. No. 8,128,649 which is hereby incorporated by reference herein in its entirety.

BACKGROUND OF THE INVENTION

1. Field of the Invention

The invention relates to surgical scissors instruments and, more particularly, to endoscopic scissor instruments having small-sized scissor blades.

2. State of the Art

Endoscopy is a minimally invasive diagnostic medical procedure that is used to assess the interior of the human body using an endoscope. An endoscope generally consists of a rigid or flexible tube, an fiber optic illumination system to guide light provided by a light source through the tube of the endoscope in order to illuminate the organ or object under inspection, and a viewing system for collecting an image of the organ or object under inspection and for recording the image on an internal CCD device (video-endoscope) or for transmitting the image through the tube via a fiber optic bundle to an external video processor for viewing (fiber-endoscope). The endoscope can include one or more "operating" channels (typically 2-4•mm in diameter) that provide for passage of specialized medical instruments through the endoscope and into the field of view. Such specialized instruments (which can include biopsy forceps, brushes, needles, snares, scissors, graspers, cutters, clip appliers, etc.) can be used to take biopsies and retrieve organs (or pieces thereof) and/or foreign objects from the inside of the body. In some instruments (especially those with lateral-viewing optics), the distal tip of the operating channel incorporates a small deflectable elevator or bridge, which permits some directional control over the instrument exiting therefrom. These general principles apply to most endoscopes, but specific instruments differ in length, size, stiffness, as well as other characteristics as the instruments are typically designed for a particular application. Endoscopy can involve, for example, the gastrointestinal tract such as the esophagus, stomach and duodenum, small intestine, and colon. It can also involve the respiratory tract, the urinary tract, the female reproductive system, and the organs of the chest. It can also involve the interior of a joint (arthroscopy). Many endoscopic procedures are considered to be relatively painless and, at worst, associated with moderate discomfort.

Laparoscopy is a minimally invasive surgical technique in which operations in the abdomen or thorax are performed through small incisions (usually 0.5-1.5 cm) via a laparoscope. There are generally two types of laparoscopes, including a telescopic rod lens system that is usually connected to a video camera (single chip or three chip) and a digital laparoscope where the camera is placed at the end of the laparoscope, thus eliminating the rod lens system. A fiber optic cable system connected to a light source (halogen or xenon is inserted through a surgical port to illuminate the operative field for viewing. The abdomen is usually insufflated with carbon dioxide gas to create a working and viewing space. Specialized surgical instruments can be introduced into the abdomen or thorax through a surgical port in order to take biopsies and retrieve organs (or pieces thereof) and/or foreign objects from the inside of the body.

The specialized surgical instruments used for endoscopy, laparoscopy or arthroscopy generally include end effector means (e.g., graspers, cutters, forceps, scissors, clip appliers, etc.) mounted adjacent the distal end of a tube or coil. Handles (or other actuation control means) are mounted to the proximal end of the tube or coil and move an actuator axially through the tube or coil. The distal end of the actuator is mechanically coupled to the end effector means in a manner that transforms the axial movement of the actuator into the desired movement of the end effector means. Such specialized endoscopic, laparoscopic or arthroscopic surgical instruments are collectively referred to herein as endoscopic surgical instruments or endoscopic instruments. These general principles apply to most endoscopic instruments, but specific endoscopic instruments differ in length, size, stiffness, as well as other characteristics as the instruments are typically designed for a particular application as such instruments can be used for a wide variety of minimally invasive surgical procedures, including the endoscopic, laparoscopic and arthroscopic applications summarized above.

Endoscopic surgical scissors instruments generally include a pair of scissor blades pivotably mounted adjacent the distal end of a tube or coil. The scissor blades have sharpened edges that effect cutting of tissue during pivotal movement of the scissor blades relative to one another. Handles (or other actuation control means) are mounted to the proximal end of the tube or coil and move an actuator axially through the tube or coil. The distal end of the actuator is mechanically coupled to the scissor blades in a manner that transforms the axial movement of the actuator into pivoting movement of the scissor blades.

Endoscopic scissors instruments may be generally classified as either "single acting" or "double acting." In a single acting instrument, a stationary scissor blade is supported adjacent the distal end of the tube or coil and a movable scissor blade is coupled to the distal end of the actuator and is supported adjacent the distal end of the tube or coil for rotation relative to the stationary scissor blade in accordance with actuation transmitted by the actuator. In double acting instruments, two scissor blades are coupled to the distal end of the actuator and supported adjacent the distal end of the tube or coil for rotation relative to one another in accordance with actuation transmitted by the actuator.

The construction of the scissor blades theoretically supplies a moving contact point between the opposing cutting edges as the scissor blades are closed by their pivotable movement. In order to effect a smooth cutting action, the engaging cutting edges must be kept in a moving contact point throughout the closing of the scissor blades. Typical scissor designs usually accomplish this by the use of any of the following methods: firstly, via a mechanism or feature separated from the blades that biases the scissor blades together as the scissor blades are closed; secondly, by dimensioning the blades with a longitudinally bowed profile that forces the opposed scissor blades against each other as the scissor blades are closed and lastly by a very accurately constructed assembly with no mechanical slop in the dimensions of, or the positioning of, the scissors' blades or related components The biasing means of the first example typically is accomplished by tightening the scissors' pivot nut to remove all dimensional slop in the assembly or with a cammed surface behind the pivot area that effects biasing of the scissor blades closer together as they close over each other. In the second method, which is used most commonly for larger or longer scissor blades, such as those in a standard full-sized scissor as used in regular "open" surgery, a bowed-profile that runs along the longitudinal axis of the scissor blade forces the cutting edges together. This method gives a mostly adequate cutting performance for open style surgical scissors. However for smaller scissor blades such as those used in endoscopic devices, the total loss of resiliency, due to the stiffness of small blades, means that a bowed profile in the scissor blade will not work and will only result in the contacting cutting edges gouging each other or quickly wearing away. Therefore in the currently available endoscopic scissor devices such small non-resilient and rigid blades must be designed to maintain the edge to edge contact through the use of components with very stringent dimensional accuracies, tight tolerances and tight fits. This last design method involves difficult and costly assembly and manufacturing processes. In addition, the effects of using cams or similar features in the design of small endoscopic scissors is limited by the remoteness of the cam surface from the cutting edges and because of persistent assembly "slop" offers little improvement to the problem of maintaining edge to edge contact. These design schemes have historically failed to give small surgical scissor instruments the desired sensitive feel and cutting performance that surgeons require and are familiar with through their experience in open surgery using larger hand-held surgical scissors.

SUMMARY OF THE INVENTION

The invention provides an endoscopic scissors instrument with small-size scissor blades with improved cutting performance through an improved biasing means whereby features contained in and as part of the blade itself automatically provide a preload to its cutting edge as two scissor blades move past one another.

The invention also provides such an endoscopic scissors instrument that avoids inherently expensive components, assembly and manufacturing processes.

According to the invention, an endoscopic scissors instrument includes an elongate hollow member having a proximal end and a distal end, an actuator that moves axially through the hollow member, and first and second scissor blades with respective cutting edges. At least one of the first and second scissor blades are rotatably coupled to the hollow member adjacent its distal end. At least one of the first and second scissor blades includes a base supporting a resilient leaf-spring portion that defines a respective cutting edge. The resilient leaf-spring portion extends from the base in a cantilevered arrangement along the length of the base. The cantilevered arrangement and angling of the leaf-spring portion serves to generate a spring force acting on the respective cutting edge such that, when in a loaded state, there is an automatic preloading force imparted between the cutting edges of the scissors' blades that maintains a consistent and continuous mating force between the two opposed sharpened cutting edges, preferably over the complete range of rotational movement of the scissor.

It will be appreciated that the endoscopic scissor instrument of the present invention provides improved edge to edge preload of the opposed scissor blades and thus enables superior cutting quality and operator feel for endoscopic scissor instruments where historically it has not been available.

Additional advantages of the invention will become apparent to those skilled in the art upon reference to the detailed description taken in conjunction with the provided figures.

BRIEF DESCRIPTION OF THE DRAWINGS

FIGS. 6A and 6B are front cross-sectional views of the respective scissor blades of the instrument of FIGS. 1-3 along section lines similar to 5B-5B in FIG. 5A which illustrate the relief angles of the cutting features of the respective scissor blades relative to the corresponding blade supports in accordance with the present invention; the cross hatching of the section is omitted to more clearly show the relief angles depicted therein.

DETAILED DESCRIPTION OF THE PREFERRED EMBODIMENT

For purposes herein, the "distal end" of a surgical instrument or any part thereof, is the end most distant from the surgeon and closest to the surgical site, while the "proximal end" of the instrument or any part thereof, is the end most proximate the surgeon and farthest from the surgical site.

Figure 1:
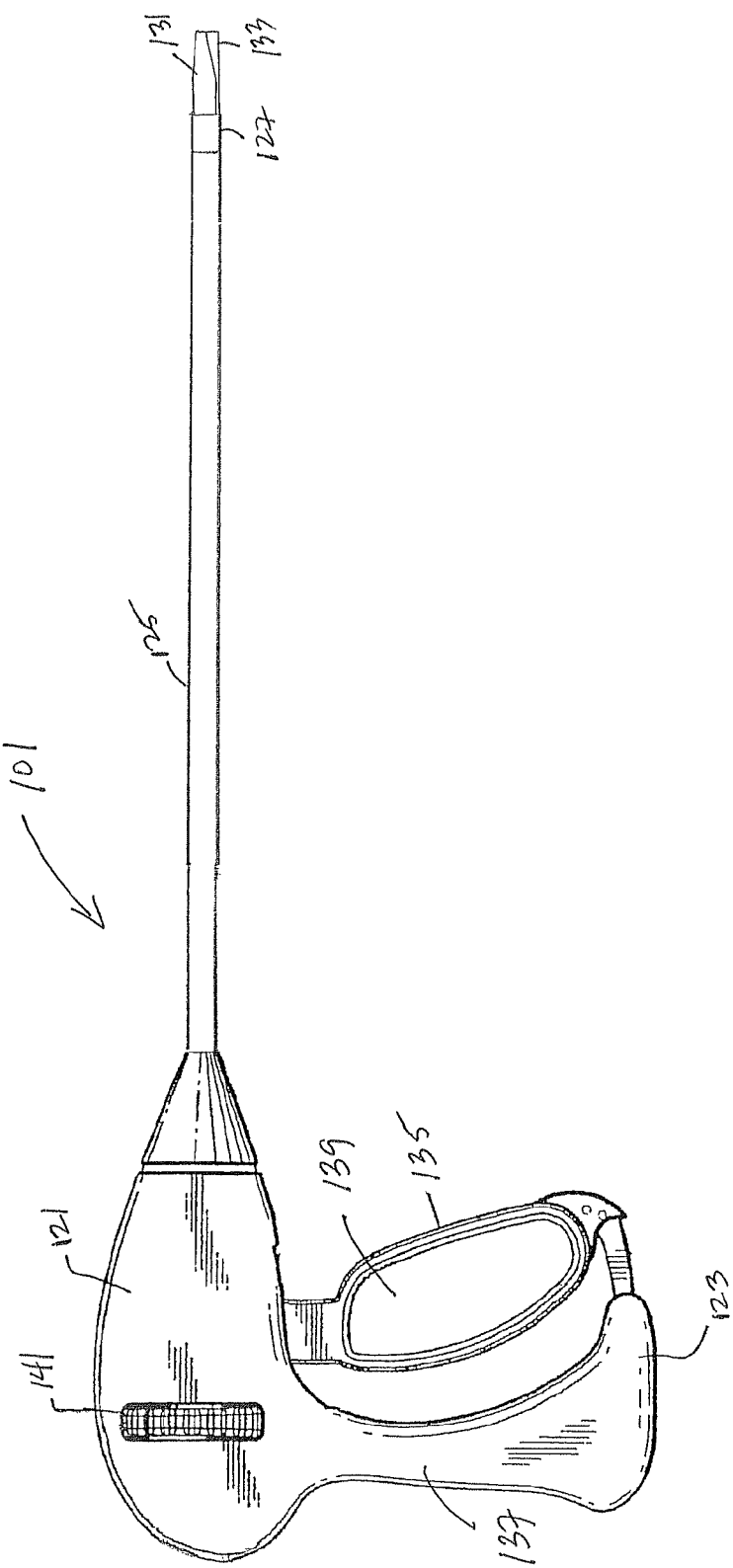
FIG. 1 is a side view of an exemplary endoscopic scissors instrument that embodies the present invention.
Figure 2:
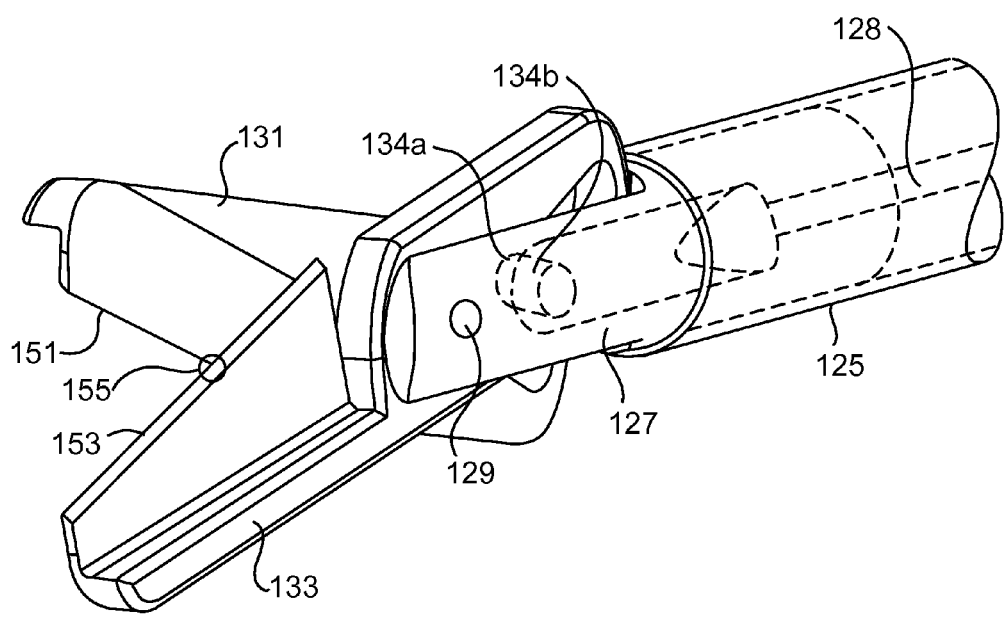
FIG. 2 is an isometric view of the distal portion of the endoscopic scissors instrument of FIG. 1 in accordance with the present invention where the scissor blades of the instrument are positioned in an open configuration.

Turning now to FIGS. 1 and 2, an exemplary endoscopic scissors instrument 101 in accordance with the invention includes a housing 121 for supporting a handle assembly 123. A hollow tubular member 125 is provided with a proximal end fixably coupled to the housing 121 and a distal end fixably coupled to a clevis 127. The hollow tubular member 125 can be a coil to provide for bending and flexibility or can be a rigid or operator plastically deformable tube. A push rod actuator 128 extends through the hollow tubular member 125 to the clevis 127. The push rod actuator 128 is coupled to a pair of scissor blades 131, 133 via linkages, cams 134a, 134b, or other suitable coupling features and the scissor blades 131, 133 are rotatably mounted in the clevis 127 by a pivot post 129. In this configuration, axial movement of the push rod actuator 128 within the hollow tubular member 125 causes the scissor blades 131, 133 to rotate around the post 129 and thus pivot relative to one another. Additional details of the hollow tubular member 125, the clevis 127, and the push rod actuator 128 may be obtained by reference to U.S. Pat. No. 5,192,298 to Smith et al., herein incorporated by reference in its entirety. It will also be appreciated that other actuating mechanisms and other mechanisms for causing rotation of the scissor blades could be utilized for the endoscopic scissors instrument of the invention. Indeed, rather than using a clevis with a post around which the scissor blades rotate, the scissor blades could be provided with arcuate grooves as disclosed in U.S. Pat. No. 4,712,545 to Honkanen, herein incorporated by reference in its entirety. The invention applies to single acting and double acting endoscopic surgical scissors. It will be appreciated by those skilled in the art that other mechanisms for linking the actuation mechanism to the scissor blades 131, 133 may be utilized, such as links and pins, or a pin riding in cammed slots, or other suitable actuating mechanism. Indeed, if desired, in a single acting instrument, the push rod or actuating wire could be directly connected to the scissor blade, and in double acting instruments, two connected push rods or actuating wires could be utilized for direct connection to the scissor blades.

In the illustrative embodiment, the handle assembly 123 includes a movable front handle 135 and a fixed rear handle 137. The front handle 135 has an aperture 139 defined therethrough which enables a user to grasp and move the front handle 137 relative to the rear handle 137. More particularly, front handle 135 is selectively moveable by the user from a first position offset from the rear handle 137 to a second position in closer proximity to the rear handle 137. Such movement is transmitted to axial movement of the push rod actuator 128 extending through the hollow tubular member 125 in order to impart pivotal movement of the scissor blades 131, 133 relative to one another. A control wheel 141 can be supported within the housing 121 and extend through sidewalls of the housing 121 to allow the user to rotate together the hollow tubular member 125, the clevis 127 and the scissor blades 131, 133 mounted thereto or to rotate the clevis 127 and the scissor blades 131, 133 independently of and separately from, the hollow tubular member 125.

Figure 3:
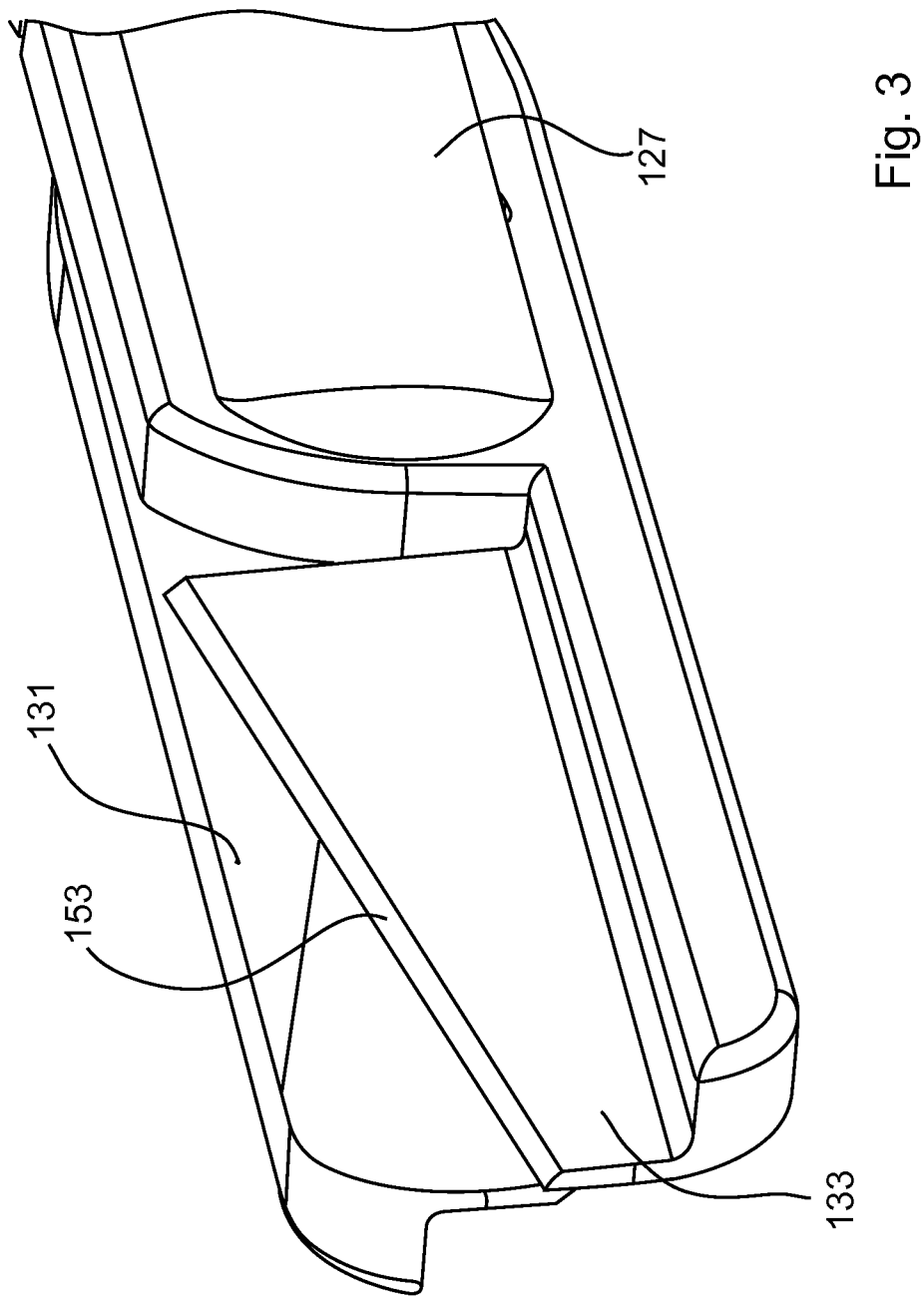
FIG. 3 is an isometric view of the distal portion of the endoscopic scissors instrument of FIG. 1 in accordance with the present invention where the scissor blades of the instrument are positioned in a closed configuration.

As shown in FIGS. 2 and 3, each of the scissor blades 131, 133 is provided with an inside cutting edge 151, 153 that contact one another as the scissor blades 131, 133 pivotably rotate relative to one another during use. During such rotation, a point of contact of the cutting edges 151, 153 moves along the cutting edges. In an open configuration, the point of contact is nearer to the pivot point or clevis (FIG. 2). As the blades close, the point of contact moves further from the pivot point or clevis (FIG. 3). In FIG. 2, the scissor blades 131, 133 are shown in an open configuration where the cutting edges 151, 153 are in bearing contact near the pivot point at a point shown generally by the circled portion 155.

Figure 4B:
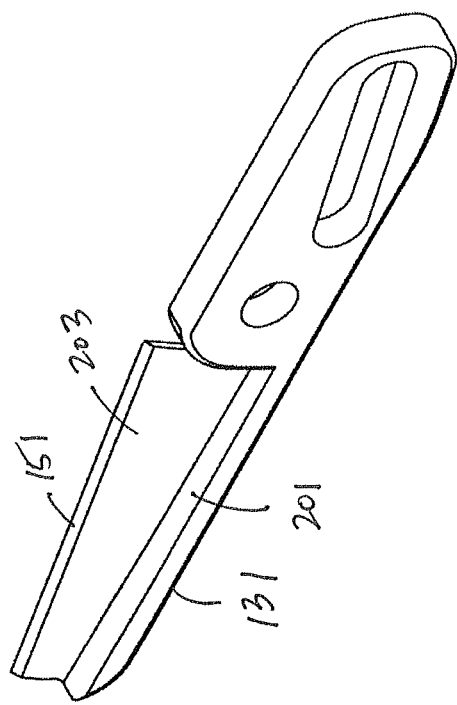
FIGS. 4A and 4B are schematic views of the scissor blades of the endoscopic scissors instrument of FIGS. 1-3 in accordance with the present invention.
Figure 4A:
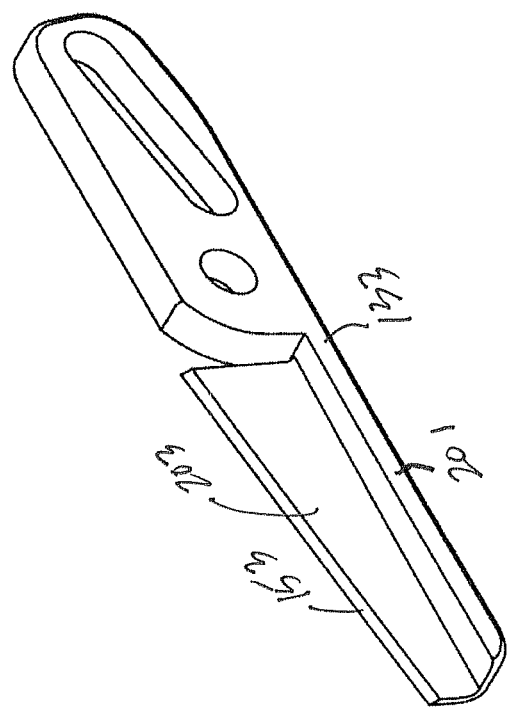

FIGS. 4A and 4B show a schematic view of scissor blades 131, 133, each of are realized by two unitary parts 201, 203. The first part 201, referred to herein as a "blade support", is thicker and stiffer than the second part 203, referred to herein as a "cutting feature." The thin cutting feature 203 includes a sharpened cutting edge (151,153) that extends along the entire length of the top edge of the cutting feature 203 preferably with a tapered profile as shown. Other profiled designs, such as a stepped profile or other variable profile can be used.

Figure 5A:
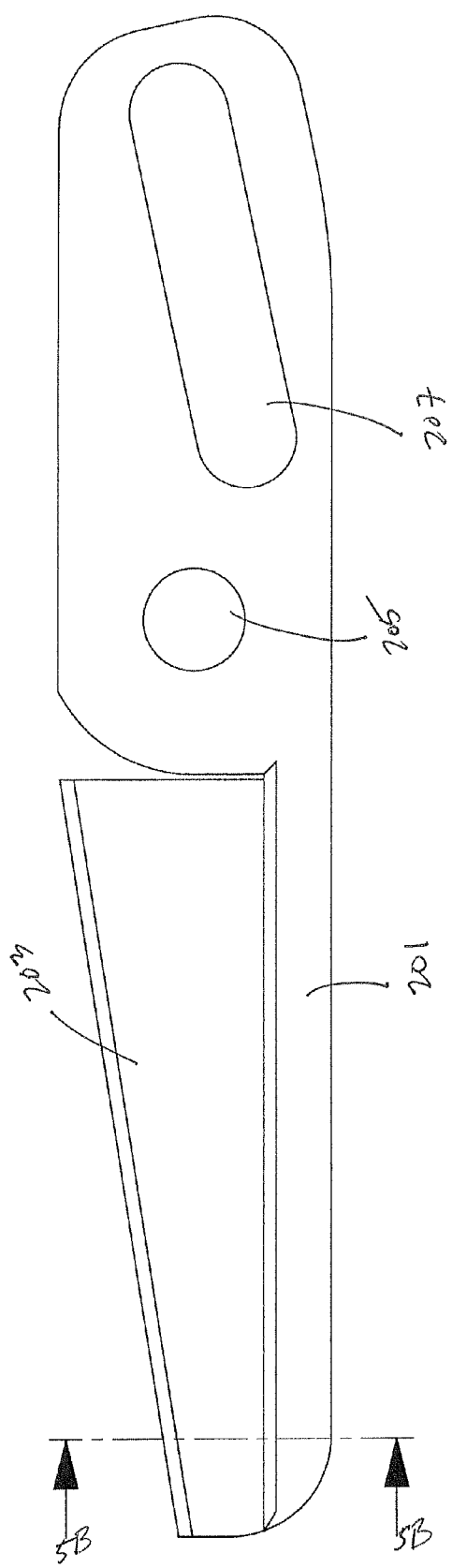
FIG. 5A is a side view of one of the scissor blades of FIGS. 4A and 4B in accordance with the present invention.

As shown in FIG. 5A, the blade support 201 includes a first side 202a adjacent a plane through which the cutting edges 151, 153 of the blades extend, and an opposite second side 202b. In addition, the blade support includes a thru-hole 205 that receives the pivot post 129 as well as a cam-slot 207 disposed proximal to the thru hole 205 and which receives a cam pin 134a or 134b connecting to the distal end of the actuator rod of the instrument. This arrangement provides for pivotal movement of the scissor blades 131, 133 relative to another in response to axial movement of the actuator rod as is well known.

Figure 5B:
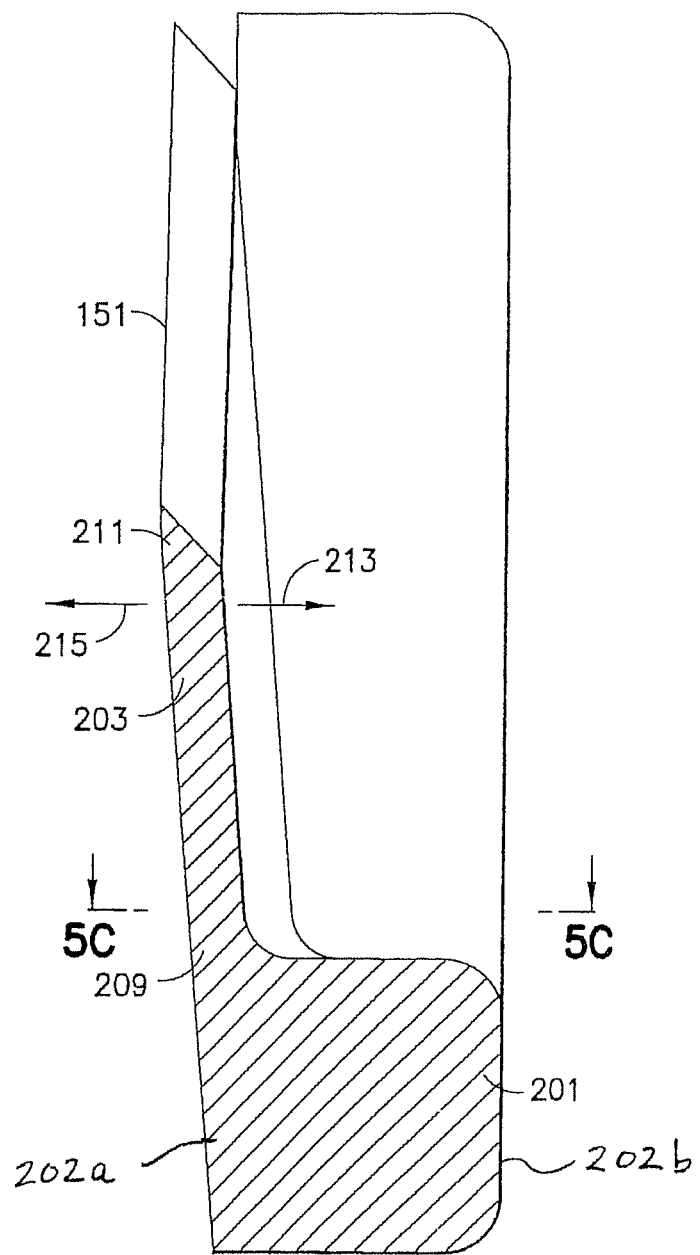
FIG. 5B is a cross-sectional view of the scissor blade of FIG. 5A along the section labeled 5B-5B in FIG. 5A.

As best shown in the cross-section of FIG. 5B, the thin cutting feature 203 of the scissor blades 131, 133 realizes a cantilever spring arrangement by fixing its bottom portion 209 to the blade support 201 with its top portion 211 angled or otherwise arranged to hold a bias along the length of the respective sharpened cutting edge (labeled 151 in FIG. 5B) that will ensure that the cutting edge intersects the opposing blade's cutting edge in a scissor assembly. In this cantilever spring arrangement, the thin cutting feature 203 acts as a resilient leaf-spring that allows for resilient deflection of the top portion 211 of the cutting feature 203 relative to its bottom portion 209 being rigidly held and positioned by the thick blade support 201. This allows one sharpened cutting edge 151 to forcibly engage with the opposing blade's cutting edge 153 in a resilient and deflective manner so no gouging or wear damages the cutting edges. Such resilient deflection is depicted by vector arrow 213 in FIG. 5B. The cantilever spring arrangement of the cutting feature 203 extends along the length of the cutting feature 203 such that the resilient deflection of the top portion 211 relative to its bottom portion 209 and the blade support 201 is provided along the entire length of the cutting feature 203. The cantilever spring arrangement of the cutting feature 203 also provides a spring moment that is primarily directed across the cutting edge of the cutting feature 203 laterally outward away from the blade support 201 in the direction of vector arrow 215 as shown in FIG. 5B.

Figure 6C:
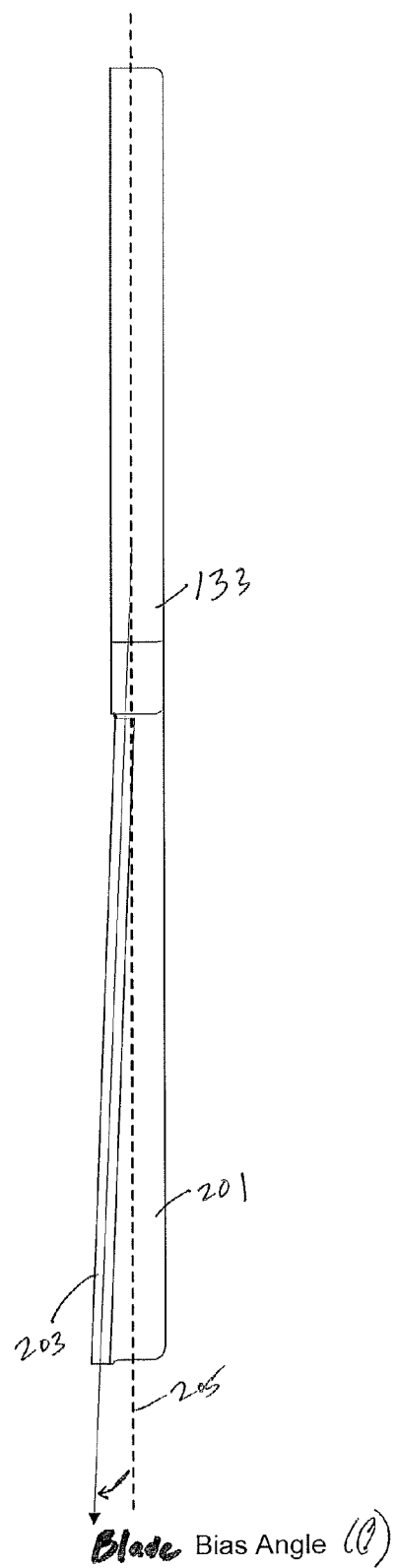
FIG. 6C is a cross-sectional view of the scissor blade of FIG. 6B along the section labeled 6C-6C in FIG. 6B which illustrates the blade bias angle of the cutting feature of the respective scissor blade relative to its blade supports in accordance with the present invention; the cross hatching of the section is omitted to more clearly show the blade bias angle depicted therein.

The cantilever spring arrangement and positional bias of the cutting features 203 ensure that the cutting edges 151, 153 of the two blades 131, 133 are in intersecting planes as the blades 131, 133 are closed. In the preferred embodiment as illustrated in FIGS. 6A-6C, the opposed cutting features 203 extend from respective base supports 201 at a relief angle $\alpha$ relative to the rotational planes 205 of the respective scissor blades. Moreover, as best shown in FIG. 6C, the lengthwise profile of the respective cutting features 203 of the scissor blades are angled at a blade bias angle $\beta$ relative to the rotational planes 205 of the scissor blades. The bias angle of the cutting features of the two blades point toward one another as is evident from FIGS. 6A and 6B. In an illustrative embodiment, the relief angle a of the cutting features is in the range between 3° and 7° (more preferably on the order of)5° and the blade bias angle $\beta$ of the cutting features is in the range between 0.5° and 3° (more preferably on the order of 1.5°). Importantly, the relief angle $\alpha$ and the blade bias angle $\beta$ of the cutting features 203 are provided such that selectively only the cutting edges 151, 153 of the two blades 131, 133 are on intersecting planes and therefore edge to edge contact one another is insured as the blades 131, 133 are closed. These design aspects of the leaf-spring provide a necessary blade-to-blade preload force as the blades 131, 133 are closed, which maintains a consistent and continuous forceful contact of the two opposed cutting edges 151, 153 over the complete range of rotational movement of the scissor blades 131, 133. Using this design strategy enables a small scissor to use components and manufacturing techniques with much lower quality standards without need of the high tolerance and ultra fine positioning that is presently required in surgical scissors while elevating the cutting ability and feel to a level beyond that of existing endoscopic and other small surgical scissors.

Figure 5C:
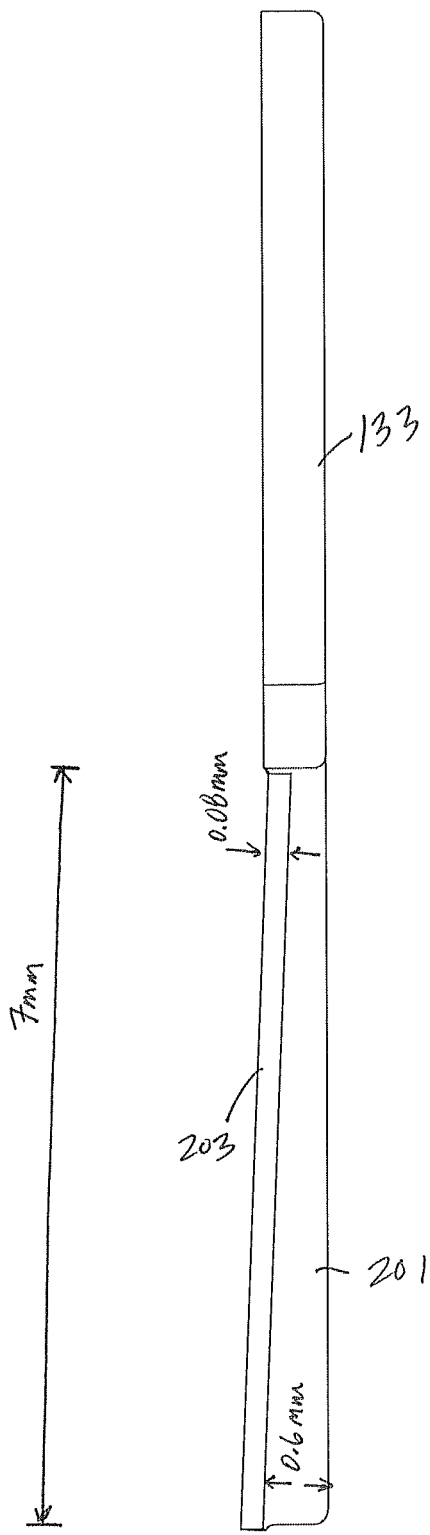
FIG. 5C is a cross-sectional view of the scissor blade of FIGS. 5A and 5B along the section labeled 5C-5C in FIG. 5B.

In the preferred embodiment, the blade support 201 of the respective blade has a thickness between 0.25 mm and 5 mm, while the cutting feature 203 of the respective blade has a thickness between 0.05 mm and 0.5 mm and a length less than 50 mm and preferably a range between 5 mm and 20 mm. FIG. 5C illustrates an exemplary embodiment where the blade support 201 has a maximal thickness of 0.6 mm, and the cutting feature 203 has a thickness of 0.08 mm and a length of 7 mm. In the preferred embodiment, the scissor blades 131, 135 (including the cutting features 203 of the respective blades) are realized from high tensile strength stainless steel such as high chrome alloys.

Advantageously, the endoscopic scissor instrument of the present invention provides an improved automatic edge to edge preload of the opposed scissor blades while avoiding the problems associated with a bowed blade profile and biasing cams used in the prior art, and thus enables superior cutting quality for endoscopic scissor instruments where historically it has not been available.

Figure 7:
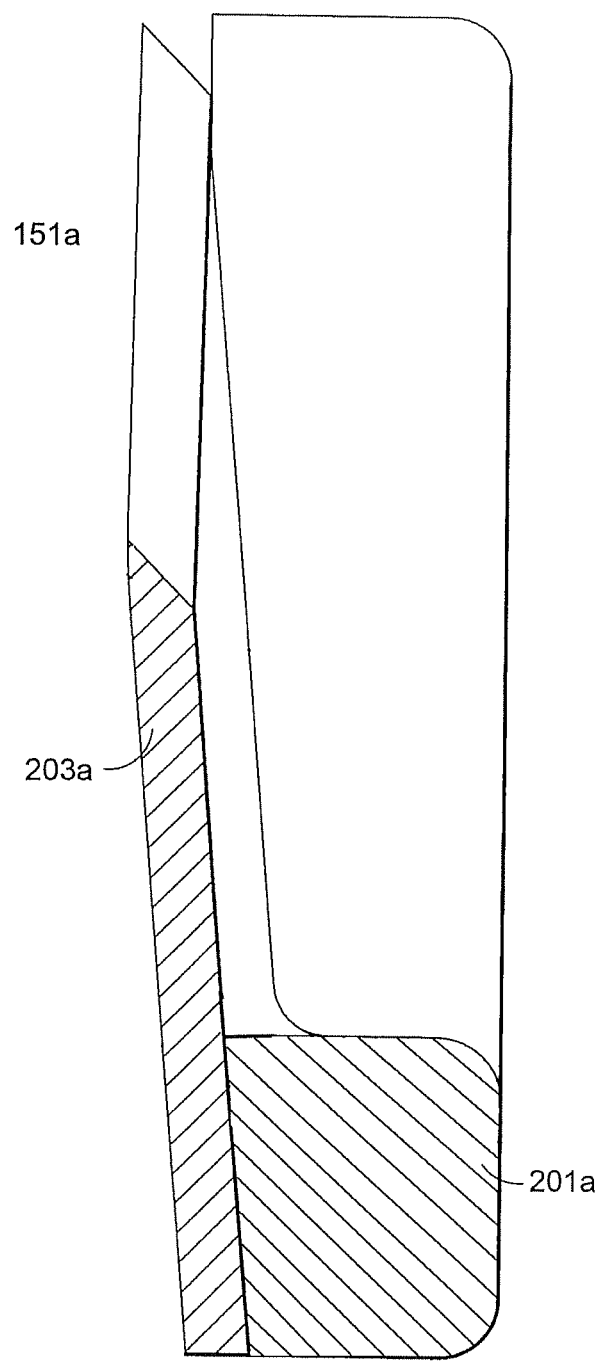
FIG. 7 is a view similar to FIG. 5B of an alternate embodiment of the invention.

There have been described and illustrated herein scissors instruments with improved scissor blades. While particular embodiments of the invention have been described, it is not intended that the invention be limited thereto, as it is intended that the invention be as broad in scope as the art will allow and that the specification be read likewise. Thus, while the surgical scissors instrument illustrated herein for exemplary purposes were double acting scissors where both blades pivot relative to each other, it will be recognized that the invention can be applied to a single acting scissors with one blade fixed and the other blade pivoting relative to the fixed blade. It may also be applied to a scissors where only one blade incorporates the present invention coupled with a standard rigid opposing blade. Also, while particular actuation mechanisms were described for causing the pivoting of the scissor blades, it will be appreciated that other mechanism could be utilized. Thus, for example, the instrument could be a flexible instrument with an outer tube formed from a coiled element which could be used through an endoscope channel or a rigid instrument with a relatively stiff outer tube of structural plastic or tubular metal which could be used through a laparoscope or arthroscope. In addition, while particular materials and dimensions have been disclosed for the scissor blades of the endoscopic scissors instruments, it will be understood that other materials and dimensions can be used. Moreover, while a particular unitary configuration of the respective scissor blades is shown, other non-unitary configurations can be used. For example, referring to FIG. 7, it is contemplated that the cutting features 203a of the respective blades (blade 151a shown) can be a separate and distinct part that is secured to the blade support 201a of the scissor blade by welding (e.g., by laser welding, spot welding, resistance welding), one or more screws or rivets, or other suitable mechanical fixation means. In this configuration, the blade support can be realized from a wide range of materials, such as a stainless steel, plastics, ceramics, etc. It will therefore be appreciated by those skilled in the art that yet other modifications could be made to the provided invention without deviating from its spirit and scope as so claimed.

What is claimed is:

1. A set of scissors blades mounted relative to each other such that at least one of the scissors blades is movable relative to the other between open and closed positions, comprising:
    a first scissors blade including a first feature with a first cutting edge; and
    a second scissors blade including
        a longitudinally extending rigid supporting base having a midline and a longitudinally extending lateral side offset relative to the midline, and
        a resilient leaf-spring portion substantially thinner than the base and having a deflectable second cutting edge that extends along a length of the leaf-spring portion, the leaf-spring portion extending from the lateral side of the base in a laterally cantilevered arrangement such that the leaf-spring portion is laterally offset from the midline of the base, and wherein as the at least one of the first and second scissors blades is moved relative to the other between open and closed positions,
    (i) the first and second cutting edges are brought into contact with each other at a contact point in an interference plane, the contact point moving along the length of the leaf spring portion as the at least one of the first and second scissors blades are moved relative to the other, and the second cutting edge resiliently deflects against the first cutting edge at the contact point,
    (ii) the leaf-spring portion generates a lateral spring force in a direction transverse to the interference plane and against the first feature of the first blade, and
    (iii) the leaf-spring portion is flat when not subject to deflection.

2. A set of scissors blades according to claim 1, wherein:
the leaf-spring portion is formed discrete from the base and coupled to the base along the length of the base.

3. A set of scissors blades according to claim 2, wherein:
the leaf-spring portion is welded to the blade support.

4. A set of scissors blades according to claim 1, wherein:
the first scissors blade includes a longitudinally extending rigid supporting base and an immediately laterally adjacent resilient, leaf-spring portion substantially thinner than the base, the leaf-spring portion forming the first feature, and the first cutting edge being deflectable, the leaf-spring portion extending laterally from the base of the first scissors blade in a laterally cantilevered arrangement along a length of the base, and longitudinally coextending with the base,
wherein the first and second cutting edges of the first and second scissors blades resiliently deflect about each other at the contact point.

5. A set of scissors blades according to claim 1, wherein:
the spring force maintains an unchanging and continuous mating force between the first and second cutting edges as the at least one of the first and second scissors blades is moved relative to the other between the open and closed positions.

6. A set of scissors blades according to claim 1, wherein:
the resilient leaf-spring portion has a thickness between 0.05 mm and 0.5 mm.

7. A set of scissors blades according to claim 1, wherein:
the resilient leaf-spring portion has a tapered profile along its lengthwise dimension.

8. A set of scissors blades according to claim 1, wherein:
the leaf-spring portion extends at both a bias angle and a relief angle, each defined relative to a rotational plane through which at least one of the first and second scissors blades is moved as at least one of the scissors blades is moved relative to the other between the open and closed positions.

9. A set of scissors blades mounted relative to each other such that at least one of the scissors blades is rotatable relative to the other between open and closed positions, comprising:
    a first scissors blade including a first feature with a first cutting edge,
    a second scissors blade including a longitudinally extending rigid supporting base and a laterally offset, resilient leaf-spring portion substantially thinner than the base,
    the leaf-spring portion extending from and immediately laterally adjacent a lateral side of the base in a laterally cantilevered arrangement along a length of the base, and longitudinally extending with the base,
        the leaf-spring portion having a second cutting edge that extends along a length of the leaf-spring portion, and the leaf spring portion extending at a bias angle and a relief angle relative to a rotational plane through which one of the first and second scissors blades is rotational relative to the other to generate a lateral mating force between the first and second cutting edges at a contact point.

10. A set of scissors blades according to claim 9, wherein:
the leaf-spring portion is formed discrete from the base and is coupled to the base along the length of the base.

11. A set of scissors blades according to claim 9, wherein:
the leaf-spring portion is welded to the blade support.

12. A set of scissors blades according to claim 9, wherein:
the first scissors blade includes a longitudinally extending rigid supporting base, and the first feature is a resilient leaf-spring portion substantially thinner than the base, the leaf-spring portion extending from a lateral side of the base of the first scissors blade in a laterally cantilevered arrangement along a length of the base.

13. A set of scissors blades mountable relative to each other such that at least one of the scissors blades is rotatable relative to the other in a scissoring action between open and closed positions, comprising:
a first scissors blade including a first feature with a first cutting edge; and
a second scissors blade including
a longitudinally extending rigid supporting base having a midline and a longitudinally extending lateral side offset relative to the midline, and
a resilient leaf-spring portion substantially thinner than the base and having a deflectable second cutting edge that extends along a length of the leaf-spring portion, the leaf-spring portion extending from the lateral side of the base in a laterally cantilevered arrangement such that the leaf-spring portion is laterally offset from the midline of the base, and extends from the lateral side of the base at both a bias angle and a relief angle relative to a rotational plane through which the mounted leaf-spring portion is rotatable, and
wherein as the at least one of the first and second scissors blades is moved relative to the other between open and closed positions,
(i) the first and second cutting edges are brought into contact with each other at a contact point in an interference plane, the contact point moving along the length of the leaf spring portion as the at least one of the first and second scissors blades are moved relative to the other, and the second cutting edge resiliently deflects against the first cutting edge at the contact point,
(ii) the bias and relief angles of the leaf-spring portion generate a lateral spring force in a direction transverse to the interference plane and against the first feature of the first blade, and
(iii) the leaf-spring portion is flat when not subject to deflection.

14. In a scissors device including first and second blade supports mounted relative to each other such that at least one of the blade supports is rotable relative to the other in a scissoring action between open and closed positions, the first blade support provided with a first feature having a first cutting edge, and the second blade support provided with a longitudinally extending rigid supporting base having a midline and a longitudinally extending lateral side offset relative to the midline, the scissors device comprising:
a resilient leaf-spring portion substantially thinner than the base and having a deflectable second cutting edge that extends along a length of the leaf-spring portion, the leaf-spring portion coupled to the second blade support to extend from the lateral side of the base in a laterally cantilevered arrangement such that the leaf-spring portion is laterally offset from the midline of the base, such that when at least one of the first and second scissors blade supports are rotated relative to the other between the open and closed positions,
(i) the first and the second cutting edges are brought into contact with each other at a contact point, the contact point moving along the length of the leaf spring portion as the first and second blade supports are rotated, and the second cutting edge resiliently deflects against the first cutting edge at the contact point,
(ii) the leaf-spring portion extends from the second blade support at both a bias angle and a relief angle relative to a rotational plane through which one of the first and second blade supports are rotatable, and thereby generates a lateral spring force in a direction transverse to the rotational plane, and
(iii) the laterally cantilevered leaf-spring portion is flat when not subject to deflection.

15. The scissors device according to claim 14, wherein:
the leaf-spring portion is formed discrete from the base.

16. The scissors device according to claim 14, wherein:
the leaf-spring portion is coupled to the base along the length of the base.

17. The scissors device according to claim 14, wherein:
the first feature of the first blade comprises a second resilient leaf-spring portion and the first cutting edge is a sharpened deflectable cutting edge of the second leaf-first portion, the second leaf spring portion coupled to extend from a lateral side of the first blade in a laterally cantilevered arrangement.

18. The scissors device according to claim 17, wherein:
the second leaf-spring portion is formed discrete from the first blade.

19. A scissors blade cutting feature for a scissors device which has first and second blade supports mounted relative to each other such that at least one of the blade supports is rotatable relative to the other in a scissoring action between open and closed positions, the first blade support provided with a first feature having a first cutting edge, and the second blade support provided with a longitudinally extending rigid supporting base having a midline and a longitudinally extending lateral side offset relative to the midline, the cutting feature comprising:
a resilient leaf-spring portion substantially thinner than the base and having a sharpened deflectable second cutting edge that extends along a length of the leaf-spring portion, the leaf-spring portion adapted to be coupled to the second blade support to extend from the lateral side of the base in a laterally cantilevered arrangement such that the leaf-spring portion is laterally offset from the midline of the base, such that when at least one of the first and second blade supports are rotated relative to the other within a rotational plane between the open and closed positions,
(i) the first and the second cutting edges are brought into contact with each other at a contact point, and the second cutting edge is adapted to resiliently deflect against the first cutting edge at the contact point, with the contact point moving along the length of the leaf spring portion as the first and second blade supports are rotated, and
(ii) the leaf-spring portion generates a lateral spring force in a direction transverse to the rotational plane, and (iii) the leaf-spring portion is flat when not subject to deflection.

20. The scissors blade cutting feature of claim 19, wherein:
the leaf-spring portion extends at both a bias angle and a longitudinal relief angle relative to the rotational plane through which the one of the first and second blade support are rotatable.

21. The scissors blade cutting feature of claim 19, wherein:
the leaf-spring portion is formed discrete from the base.

22. The scissors blade cutting feature of claim 19, wherein:
the leaf-spring portion is coupled to the base along the length of the base.

23. The scissors blade cutting feature of claim 19, wherein:
the first feature of the first blade comprises a second resilient leaf-spring portion and the first cutting edge is a sharpened deflectable cutting edge of the second leaf-first portion, the second leaf spring portion coupled to extend from a lateral side of the first blade in a laterally cantilevered arrangement.

24. The scissors blade cutting feature of claim 23, wherein:
the second leaf-spring portion is formed discrete from the first blade.

* * * * *